United States Patent [19]

Helland

[11] Patent Number: 5,431,681
[45] Date of Patent: Jul. 11, 1995

[54] COMBINATION PACING AND DEFIBRILLATING LEAD HAVING SENSING CAPABILITY

[75] Inventor: John R. Helland, Issaquah, Wash.

[73] Assignee: Pacesetter, Inc., Sylmar, Calif.

[21] Appl. No.: 125,448

[22] Filed: Sep. 22, 1993

[51] Int. Cl.$^6$ ............................................. A61N 1/05
[52] U.S. Cl. ..................................... 607/4; 607/119
[58] Field of Search ................ 128/642; 607/119–129, 607/131, 4

[56] References Cited

U.S. PATENT DOCUMENTS

| | | | |
|---|---|---|---|
| 4,280,511 | 7/1981 | O'Neill | 607/122 |
| 4,340,457 | 7/1982 | Kater | 128/635 |
| 4,365,639 | 12/1982 | Goldreyer | 607/122 |
| 4,750,494 | 6/1988 | King | 128/419 PG |
| 4,922,927 | 5/1990 | Fine et al. | 607/122 |
| 4,972,848 | 11/1990 | Di Domenico et al. | 128/785 |
| 5,002,067 | 3/1991 | Berthelsen et al. | 128/786 |
| 5,020,544 | 6/1991 | Dahl et al. | 128/784 |
| 5,179,962 | 1/1993 | Dutcher et al. | 128/785 |
| 5,203,348 | 4/1993 | Dahl et al. | 128/642 |

FOREIGN PATENT DOCUMENTS

| | | | |
|---|---|---|---|
| 2157954 | 11/1985 | United Kingdom | 607/122 |
| 2205044 | 11/1988 | United Kingdom | 607/4 |
| 2009329 | 6/1992 | WIPO | 607/122 |

Primary Examiner—William E. Kamm
Assistant Examiner—Marianne Parker
Attorney, Agent, or Firm—Harold C. Schloss

[57] ABSTRACT

A lead, for use in combination with an implanted pulse generator which may be a pacemaker or defibrillator or combination thereof. The lead can deliver an electrical charge to pace, cardiovert or defibrillate the heart, and can sense cardiac activity in the heart. The lead may include additional sensor electrodes capable of sensing electrical or physical activity in the atrial cavity. The lead allows cardioversion and/or defibrillation stimuli to be provided by a large surface area electrode which is passively implanted in the ventricle, to allow the pulse generator to provide appropriately synchronized atrial-ventricular pacing, cardioversion or defibrillation.

24 Claims, 3 Drawing Sheets

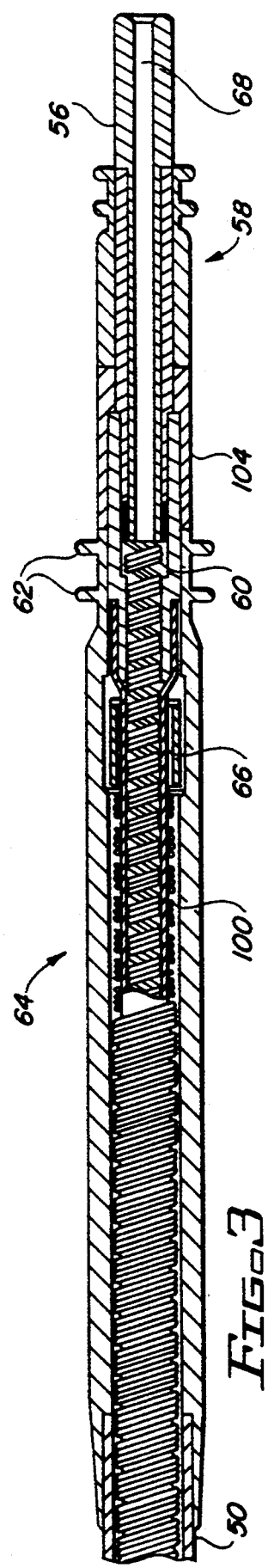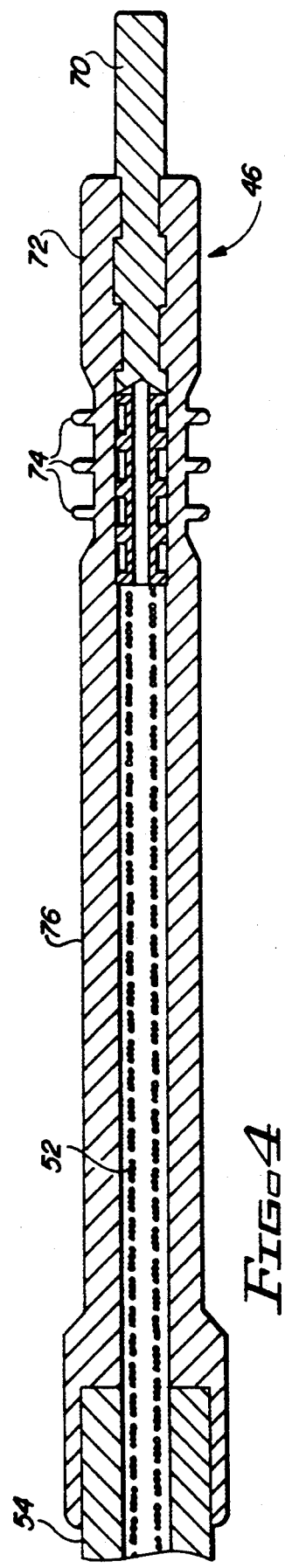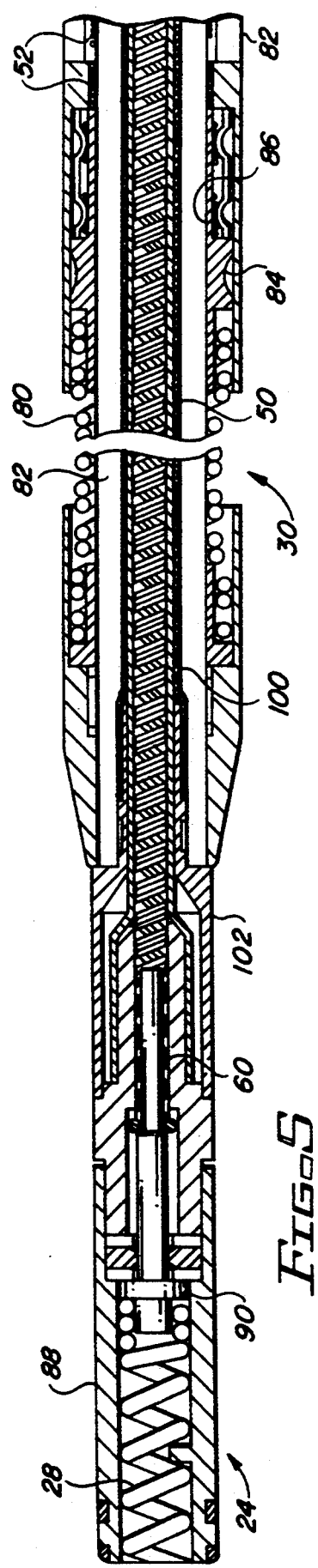

COMBINATION PACING AND DEFIBRILLATING LEAD HAVING SENSING CAPABILITY

FIELD OF THE INVENTION

The present invention relates generally to medical electronic devices and, more particularly, to implantable devices for pacing, cardioverting or defibrillating a heart. Specifically, the present invention is directed to a lead designed to be placed into the ventricle which can pace, cardiovert or defibrillate the heart, and sense cardiac activity in the heart, in conjunction with an implanted pacemaker and/or defibrillator.

BACKGROUND OF THE INVENTION

A number of types of implantable devices are in use to monitor and control the electrical activity of the heart. For example, it is known to have an implanted pacemaker interconnected via a transvenous pacing lead to an electrode in intimate contact with the myocardial tissue of the heart. The electrode can both sense the electrical activity of the heart and deliver an electrical stimulus provided by the pacemaker when required. Other systems include pacemakers and transvenous pacing leads which have a variety of sensor electrodes proximally spaced behind the tip electrode of the pacing lead. The sensors provide information to the pacemaker. There are also systems which monitor and provide automatic defibrillation utilizing an implanted power source and an electrode system, either attached to the surface of or implanted within the heart. Still other systems combine the pacemaker function with an automatic defibrillation capability, and may include multiple leads extending to internal as well as external portions of the heart.

More specifically, it is known to have a combination pacing, cardioversion, defibrillation and sensing lead implanted into the ventricle, and a large surface area patch electrode affixed to or near the exterior surface of the heart, both of which are connected to a pacemaker and/or a defibrillator. Additional pacing systems may also include a transvenously implanted lead which provides only sensing within the atrium. With this type of system, there may be two different pacing, cardioversion, defibrillation or sensor leads extending intravenously into the interior of the heart, in addition to a patch lead and electrode affixed to or near the epicardial surface of the heart, all connected to the pacemaker and/or defibrillator.

During the implantation procedure, the attending physician may implant a combination lead having pacing and sensing electrodes, which also includes a defibrillation electrode mounted proximally of the distal tip, and then test whether the defibrillation electrode can provide sufficient energy to defibrillate the heart. In the event that defibrillation requires too much energy or cannot be accomplished by the combination lead, a second lead having a patch electrode affixed to or near the epicardial surface of the heart or nearby, such as in a subcutaneous or subcostal site may be required. If such a patch electrode is also required, following affixation of the patch electrode, the attending physician may test various bipolar combinations of the leads for defibrillating the heart, using alternatively the patch electrode and/or the electrode on the combination lead as the cathode(s) or anode(s) to determine the lowest threshold for defibrillation.

Thus, while it may be necessary to have the patch electrode affixed to or near the exterior surface of the heart (or subcutaneously or subcostally near the heart), preferably if defibrillation can occur by the use of a combination pacing and defibrillation electrode placed in the right ventricle, the necessity for opening the chest cavity and affixing the patch electrode on or near the heart may be avoided.

When utilizing a pacing lead defibrillator electrode to accomplish pacing, cardioversion or defibrillation, it is important to recognize that preserving the atrial-ventricle synchronization, by proper timing of the respective contractions, is very important to prevent the patient from adverse effects resulting from asynchronous contractions. Thus, in addition to providing the necessary pacing and defibrillation charges, it is extremely beneficial to have a system which can effectively preserve synchronization of the atrial and ventricle contractions by properly sensing the atrial depolarization and properly timing the electrical stimulus to the ventricle.

One method of obtaining the additional sensory information required to provide synchronization has been through the utilization of an atrial sensing lead, to provide sensing within the atrial cavity, which provides additional information to the pacemaker. The atrial sensing lead may simply be implanted and allowed to freely float within the atrial cavity. However, the disadvantages of having a second intravenously implanted lead include the fact that more hardware is implanted, perhaps to the detriment of cardiac function and optimal blood flow, in addition to the potential problems with its placement or implant location.

Accordingly, it would be very beneficial to provide a pacing system and cardioversion or defibrillation system which utilizes an improved pacing and defibrillation lead, having the additional capability of being able to sense atrial electrical activity, thereby assisting the preservation of the atrial/ventricular synchronization while eliminating the need for an additional atrial sensing lead.

SUMMARY OF THE INVENTION

The present invention details a pacing and defibrillation lead, for use in combination with an implanted pulse generator which may be a pacemaker or defibrillator or combination thereof. The lead can deliver a variety of electrical charges to pace, cardiovert or defibrillate the heart. In addition, the lead also includes sensor electrodes capable of sensing stimuli in the ventricular cavity, including ventricular electrical activity, fluid flow, and pressure, with the use of one or more sensing electrodes. The lead allows cardioversion and/or defibrillation stimuli to be provided by a large surface area electrode located distally of the tip electrode, so as to be positioned within the ventricle, while also sensing ventricular activity, to allow the pulse generator to provide appropriately synchronized atrial-ventricular pacing, cardioversion or defibrillation.

BRIEF DESCRIPTION OF THE DRAWINGS

FIG. 3 depicts an enlarged view of a first connector at the proximal end of the lead of FIG. 1;

FIG. 4 depicts an enlarged view of a second connector at the proximal end of the led of FIG. 1;

FIG. 5 depicts the tip electrode at the distal end of the lead of FIG. 1;

DETAILED DESCRIPTION OF THE PREFERRED EMBODIMENT

Figure 1:
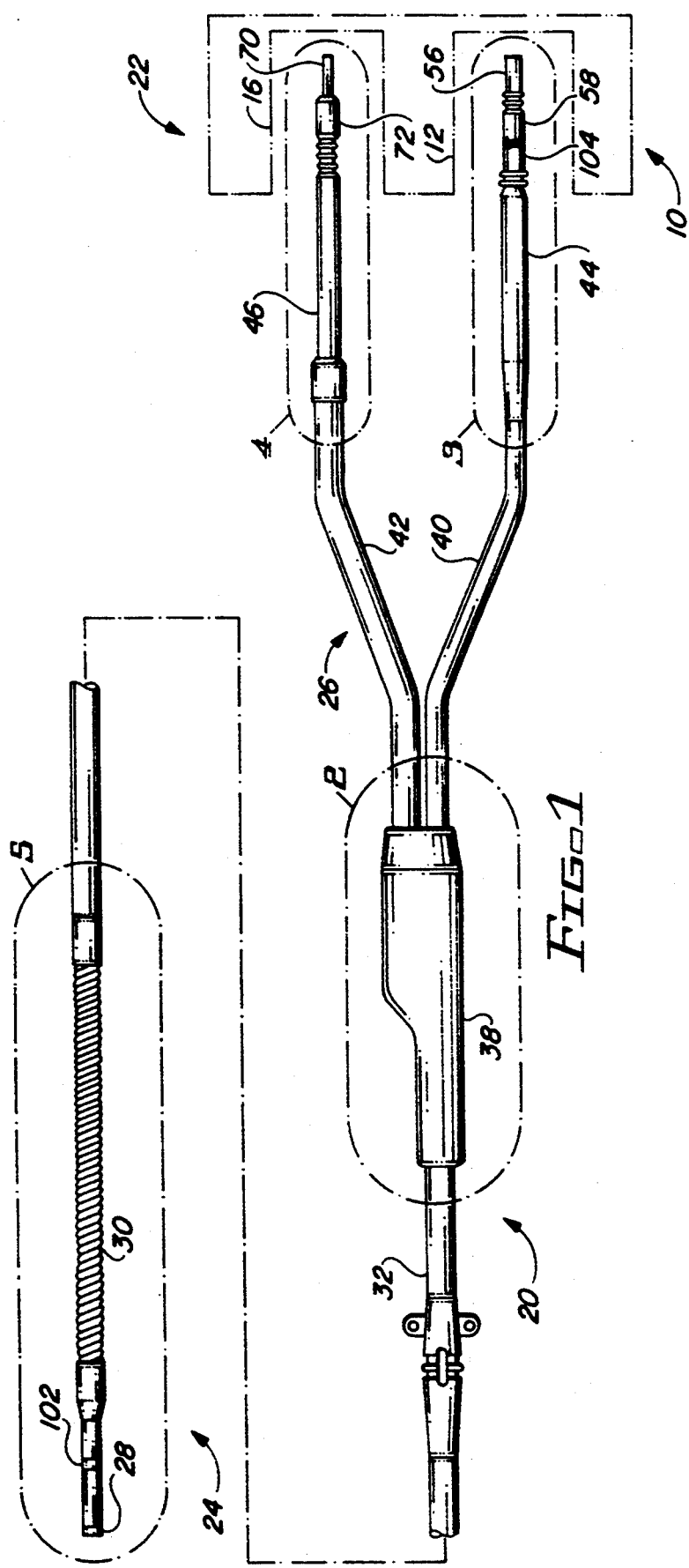
FIG. 1 depicts a pacing and defibrillation lead and pulse generator according to the present invention.

FIG. 1 depicts an implanted signal processing and pulse generator means, such as a pulse generator 10 which is preferably a pacemaker and/or defibrillator, and a pacing lead 20 according to the present invention. The pacing lead 20 includes a proximal end 22 and a distal end 24. At the proximal end 22, a connector assembly 26 accommodates interconnection with the pulse generator 10. At the distal end 24 of the pacing lead 20 is located a tip electrode 28, sensor electrode 102, and a defibrillation electrode 30. A lead body 32 interconnects the proximal end 22 and the distal end 24 of the pacing lead 20.

Figure 2:
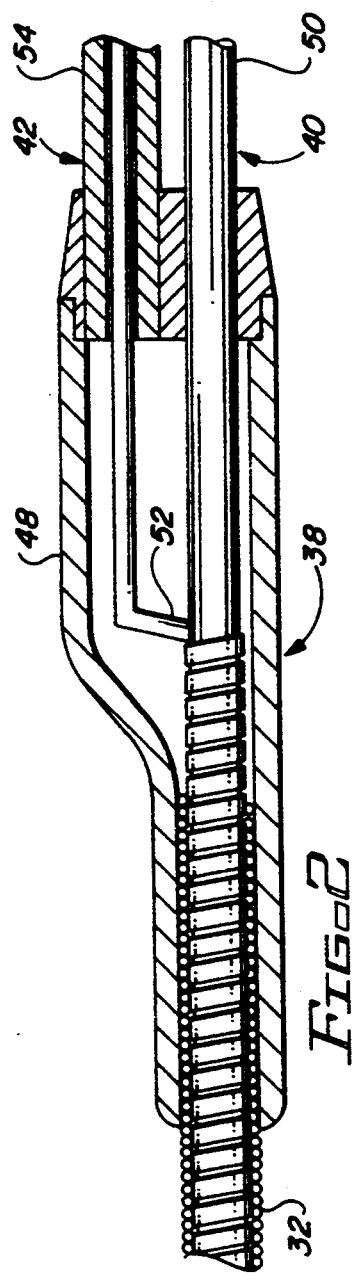
FIG. 2 depicts an enlarged view of a portion of the proximal end of the lead of FIG. 1.

The detailed construction of the proximal end 22 of the pacing lead 20, including the connector assembly 26, is illustrated in the cross-sectional views of FIG. 2-4. Initially, it is to be understood that the lead 20 of the present invention is designed for use with a variety of pulse generators 10. This is important because while the design of lead 20 is unconventional, the capability to function as a pacing lead and as a defibrillation electrode allow substitution for prior designs using multiple leads.

Generally, the pulse generator 10 has a first connector port 12 for receiving a connector means of a pacing lead having a pacing electrode at its distal end and a pin-type electrical connector at the proximal end. This first connector port 12 may also include electrical contacts for receiving electrical signals from sensor electrodes on the lead 20, which are interconnected via conductors to electrical contacts on the connector means. The electrical contacts are preferably spaced distally of the pin connector for the pacing electrode.

The pulse generator 10 may also include a second connector port 16 adapted to receive a connector means for a lead extending to a defibrillation electrode. The defibrillation lead generally includes a pin type connector which plugs into a receiving sleeve in the second connector port 16.

In view of the construction of the pulse generator 10, the connector assembly 26 of the pacing lead 20 includes a divider boot 38, which allows the lead 20 to split into two segments 40 and 42, which terminate at connector means such as first connector 44 and a second connector 46, respectively. The first connector 44 plugs into the first connector port 12, and is therefore connected to the pacing electrode. The second connector 46 plugs into the second connector port 16 and is therefore connected to the defibrillation electrode.

The divider boot 38 is shown in the partial cross sectional view of FIG. 2. The divider boot 38 includes an encasement 48 of biocompatible material which is securely affixed about the lead body 32 at one end, and is affixed about both of the segments 42 and 44 at an opposite end. Within the divider boot 38, a defibrillation conductor 52 is illustrated as being wrapped about insulation material 50 which encases the remaining conductors (not shown), at the distal side of the divider boot 38. However, midway along the length of the divider boot 38, the defibrillation conductor 52 diverges, and continues proximally within an insulator 54, to form the segment 42 which terminates at the second connector 46.

The segment 40 extends from the divider boot 38 and terminates at the first connector 44, as depicted in FIG. 3. The first connector 44 includes a connector pin 56 extending into a connector boot 58. The connector pin 56 is securely interconnected to a pacing conductor 60, which terminates at the distal end of the lead 20 at the tip electrode 28 (FIG. 1). The sensor electrode 102 is preferably at least one ring electrode. The connector boot 58 is preferably formed from a biocompatible plastic or elastomeric material such as, for example, silicon, and may include a plurality of sealing rings 62 and a connector grip area 64 extending a short distance from the connector pin 56.

The conductor 60 is encased in an insulation material 66. The conductor 60 is preferably a helically wound coil of multifilar conductors which are braided about a silver core (not shown). The helically wound coil defines a hollow central portion, extending through the center of the helix, which is in open communication with an axial bore 68 in the connector pin 56, allowing for the insertion of a stylet or guidewire (not shown) useful for allowing the proper implanting of the pacing lead 20.

The second connector 46 is shown in the detailed cross sectional view of FIG. 4. The second connector 46 includes a connector pin 70 extending into a connector boot 72. The connector pin 70 is securely interconnected to the defibrillation conductor 52. The connector boot 72 is preferably formed from a biocompatible plastic or elastomeric material such as, for example, silicon, and may include a plurality of sealing rings 74 and a connector grip area 76 extending a short distance from the connector pin 70. The defibrillation conductor 52 transitions from being encased in the insulation material 54 into the connector boot 72. The defibrillation conductor 52 is preferably helically wound, and has multifilar conductors which are braided about a silver core (not shown).

FIG. 5 depicts an enlarged cross-sectional view of the distal end 24 of the pacing lead 20. In FIG. 5, the defibrillation electrode 30 is illustrated as being a coil 80 wrapped about the insulation material 50 which encases the pacing conductor 60. Preferably, the coil 80 of the defibrillation electrode 30 is formed from a platinum-iridium wire. The coil 80 is electrically connected to the defibrillation conductor 52 at the proximal end of the coil 80, via a connector element 84. The connector element 84 also securely interconnects the defibrillation electrode coil 80, to the insulation sleeve 82 encasing the conductor 52, as well as to the insulation material 50 about which the coil 80 is wrapped. The connector element 84 includes an axial bore 86 through which the remainder of the lead body components pass prior to entering the central portion of the coil 80.

At the distal end 24 of the lead 20, the tip electrode 28 is shown retracted into a sleeve 88. The sleeve 88 is preferably formed from a silicone rubber material. The tip electrode 28 is preferably an active fixation corkscrew or helix electrode which is advanceable from the end of the sleeve 88. The tip electrode 28 is affixed to a conductive element 90. The conductive element 90 is also securely affixed to the pacing conductor 60 extending axially through the defibrillation coil 80 and insulation sleeve 50 of the defibrillation electrode 30, and through the lead body 32 to the first connector 44.

Figure 6:
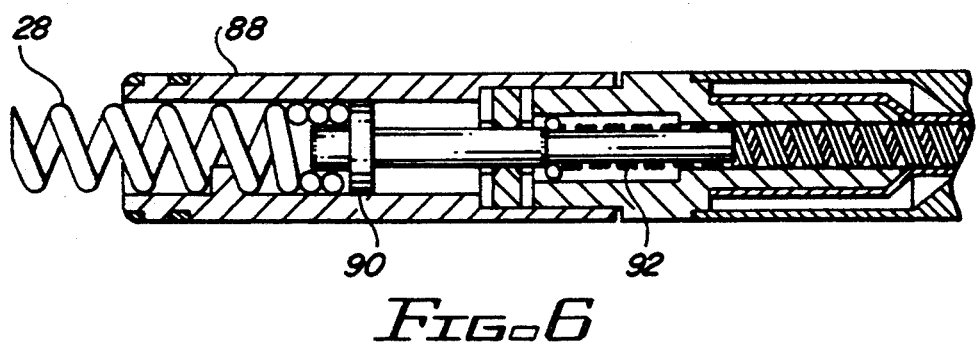
FIG. 6 depicts a view of the tip electrode of FIG. 5 wherein the helical tip electrode is extended.

FIG. 6 depicts the tip electrode 28 extended or advanced from the sleeve 88, as it would be following implantation. The tip electrode 28 may be advanced by the physicians rotation of the connector pin 56 (FIG. 3) which causes the entire pacing conductor 60 to rotate. Alternatively, a stylet (not shown) may be inserted axially through the lead 20 to rotationally advance the tip electrode 28.

Returning to FIG. 5, a third conductor such as a sensor conductor 100 may extend the length of the lead body 22, to interconnect a sensor electrode 102 and an electrical contact 104 in the first connector 44. The sensor electrode 102 is preferably located between the defibrillation electrode 30 and the sleeve 88. The first connector 44 further includes a ring connector 104 electrically connected to a sensor conductor 100, which terminates at the distal end of the lead 20 at the sensor electrode 102 (FIG. 1). The sensor electrode 102 is spaced from the defibrillation electrode 30 a distance of between 1 and 5 centimeters. Following implant of the pacing lead 20, the defibrillation electrode 30 will be positioned within the ventricle, as will the sensor electrode 102.

For any of the foregoing embodiments, the defibrillation electrode 30 may include a coating deposited on the coil 80, the material for the coating being platinum black, carbon, titanium or titanium nitride. The defibrillation electrode 30 has a total surface area in the range of between about 0.5 and 10 square centimeters, with a preferred size of between 2 and 4 square centimeters.

In addition or in the alternative, the tip electrode 28 and/or the defibrillation electrode 30 may be coated with a biocompatible, hypo-inflammatory material. Preferred biocompatible, hypo-inflammatory materials which can be used as coatings include soluble starches such as amylodextrin and amylogen, proteins such as collagen, albumin and gelatin. These protein materials may be cross-linked with a crosslinking agent such as 1-ethyl-3-(3-dimethylaminopropyl), carbodiimide, hydrochloride. Additionally, ion exchange materials such as polyethylenimine, poly-sodium styrenesulfonates, and sulfonated polytetrafluoroethylene sold under the tradename NAFION by the DuPont Corporation. These materials are preferred because of the ability of the body to resorb them without adverse effect.

Polymeric systems including polyethylene oxide or glycol, polypropylene oxide or glycol, polypropylene glycol, polysorbates, poly-vinylalcohol, and copolymers of ethylene oxide/propylene oxide can also be used as the coating material, and can deliver therapeutic agents by co-dissolution due to the inherent solubility of these materials.

The coating material is preferably a mixture of one of the above materials blended with an anti-inflammatory agent such as fluoro-trihydroxy-methyl pregna diene/d-ione or fluoro-methylprednisolone, sodium phosphate, the sodium salt of methoxy-methylnaphthalene-acetic-acid, sodium or the sodium salt or forms of dexamethasone sodium phosphate of isobutylphyl-propionic acid. The anti-inflammatory agents can constitute between about 1% to 95% by weight of the coating material, preferably however, the anti-inflammatory agents constitute in the range of between 5% and 50% by weight of the coating material.

Figure 7:
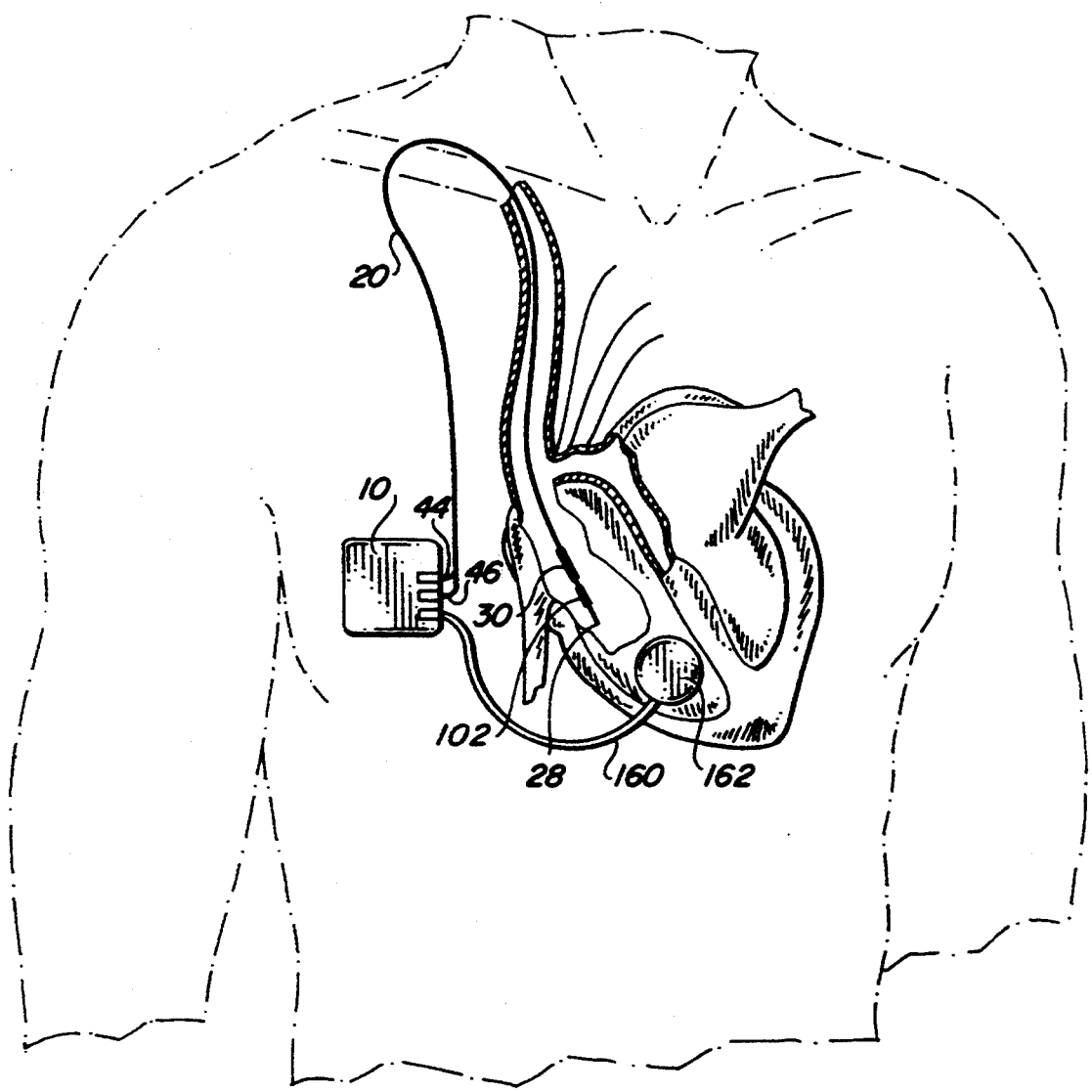
FIG. 7. depicts an implanted pulse generator interconnected via plural leads, including the lead of FIG. 1, to a heart.

FIG. 7 depicts a partially cut-away view of an implanted signal processing and pulse generating means such as the pulse generator 10 interconnected via lead 20, and a patch electrode lead 160 to a heart. The lead 20 is illustrated as being transvenously inserted and extending to the right ventricle. The pacing lead 20 includes an electrode assembly which includes the tip electrode 28 in combination with a coil type defibrillation electrode 30. The tip electrode 28 is preferably used with the pulse generator 10 to provide a pacing electrical output to the heart, and also to sense normal pacing electrical activity, in either a unipolar or bipolar arrangement. If a bipolar arrangement is used for pacing, the tip electrode 28 may act as the cathode with the defibrillation electrode 30 acting as the anode. For defibrillation, the defibrillation electrode 30 of the lead 20 may act as the cathode with the tip electrode 28 acting as the anode.

As further illustrated in FIG. 7, the patient may also have the patch electrode lead 160, which terminates at a patch electrode 162 affixed to the epicardial surface of the heart, to provide a large electrode useful for acting as either the anode or cathode in a unipolar or bipolar cardioversion or defibrillation. It may also be placed near the heart in a subcostal or subcutaneous site. The patch electrode lead 162 is also interconnected to the pulse generator. For a patient which is equipped with both of the leads depicted in FIG. 7, it may be appreciated that cardioversion or defibrillation can be accomplished by any combination of the primary electrodes, including the tip electrode 28 of lead 20, the defibrillation electrode 30 or the patch electrode 162 of patch electrode lead 160. While given a sufficient charge, any combination of the foregoing primary electrodes would operate to defibrillate a heart, a key aspect of minimizing the battery drain required for a defibrillation or cardioversion requires that the attending doctor determine which combination of electrodes will result in the lowest current threshold required for defibrillation. Thus, the doctor may sequentially test the defibrillation threshold using each of the major electrodes successively as the cathode and/or anode.

In view of the foregoing detailed description, the present invention contemplates a method of delivering an electrical stimulus to a heart. The method includes implanting a pulse generator, implanting a pacing lead extending through a vein and terminating at a tip electrode positioned within the ventricle abutting or extending into the myocardium of the heart, sensing the electrical activity of the heart, and delivering an electrical charge generated by the pulse generator through the pacing lead and the defibrillation electrode 30 to the heart. The method further contemplates delivering the electrical stimulus so as to maintain ventricular-atrial synchronization. Additionally, the method also contemplates sensing atrial activity utilizing sensor electrodes located on the pacing lead proximally spaced from the defibrillation electrode.

The foregoing methods may also require affixing a patch electrode to the epicardial surface of the heart or placing it subcostally or subcutaneously and interconnecting the patch electrode to the pulse generator, and operating the defibrillation electrode and the patch electrode in cooperation with the pulse generator as a bipolar charge delivery system to pace, defibrillate or cardiovert the heart.

It should be evident from the foregoing description that the present invention provides many advantages over leads and pacing or defibrillating systems of the prior art. Although preferred embodiments are specifically illustrated and described herein, it will be appreciated that many modifications and variations of the present invention are possible in light of the above teaching to those skilled in the art. It is preferred, therefore, that the present invention be limited not by the specific disclosure herein, but only by the appended claims.

What is claimed is:

1. An apparatus for pacing, cardioverting or defibrillating a heart comprising:
   an implantable pulse generator; and
   a lead connected at a proximal end to said pulse generator, said lead having an active fixation pacing electrode at its distal tip, a defibrillating electrode positioned proximally of said distal tip and a sensor electrode positioned between said pacing electrode and said defibrillation electrode, wherein said sensor electrode is spaced from the defibrillation electrode a distance of between 1 and 5 centimeters and wherein said lead includes means for electrically interfacing said sensor, pacing, and defibrillation electrodes with said implantable pulse generator.

2. The apparatus of claim 1, wherein said moans for electrically interfacing comprises:
   at least three electrical contacts located at the proximal end of the lead; and
   a lead body including at least three conductors having proximal and distal ends, said conductors encased within an insulation material, each of said conductors being electrically connected at a proximal end thereof to a respective one of said at least three electrical contacts and at a distal end thereof to a respective one of said sensor electrode, pacing electrode or defibrillation electrode.

3. The apparatus of claim 2, wherein said conductor attached to said defibrillation electrode is a multifilar coil made up of more than one wire of a noncorroding conductive alloy with a silver core.

4. The apparatus of claim 1, wherein said defibrillation electrode comprises an electrically conductive coil wrapped around an insulating sleeve.

5. The apparatus of claim 4, wherein said coil is formed from a platinum-iridium wire.

6. The apparatus of claim 4, wherein said coil of said defibrillation electrode includes a coating deposited on the coil, said coating being a material selected from the group consisting of platinum black, carbon, titanium and titanium nitride.

7. The apparatus of claim 1, wherein said sensor electrode senses electrical parameters of said heart, said sensor electrode comprising at least one ring electrode.

8. The apparatus according to claim 7, wherein said lead further comprises;
   a pacing conductor extending to said pacing electrode;
   a defibrillation conductor extending to said defibrillation electrode;
   a first connector assembly including a connector attached to said pacing conductor, said connector adapted for insertion into said pulse generator; and
   a second connector assembly including an electrical connector, said second connector having said electrical connector interconnected to said defibrillation conductor, said lead body forming a "Y" near its proximal end so as to merge segments connected to said first and second connector assemblies into a single lead body.

9. The apparatus of claim 8, wherein at least one of said electrodes is coated with a biocompatible, hypoinflammatory material.

10. The apparatus of claim 9, wherein said coating material is a material selected from the group consisting of hydrogels, polymeric systems, soluble starches, proteins and ion exchange materials.

11. The apparatus of claim 1, wherein said means for electrically interfacing comprises:
    a pacing conductor extending from a proximal end to a distal end connected to said pacing electrode;
    a defibrillation conductor extending from a proximal end to a distal end connected to said defibrillation electrode; and
    a divided connector assembly comprising:
       a first connector assembly including an electrical connector electrically attached to said proximal end of said pacing conductor; and
       a second connector assembly having an electrical connector electrically attached to said proximal end of said defibrillation conductor.

12. The apparatus of claim 11, wherein said first connector assembly includes an electrical sensor connector on said first connector assembly, said electrical sensor connector being electrically connected to a sensor conductor extending to said sensor electrode.

13. The apparatus of claim 12, wherein said pacing conductor and said sensor conductor are helically wound conductors separated by an insulator, said conductors defining an internal passageway allowing insertion of a stylet for aiding implantation of the lead.

14. The apparatus of claim 1, wherein said defibrillation electrode has a total surface in the range of between about 0.5 and 10 square centimeters.

15. The apparatus of claim 1, wherein said defibrillation electrode generates an electrical signal indicative of electrical activity in the heart.

16. The apparatus of claim 1, wherein said sensor electrode senses physical parameters of said heart, said sensor electrode comprising at least one ring electrode.

17. A lead adapted for connection to an implantable pulse generator, said lead comprising:
    a lead body having a proximal end and a distal end;
    a connector located at said proximal end of said lead body, said connector adapted to interconnect to said pulse generator;
    a defibrillation electrode positioned near said distal end of said lead body;
    an active fixation pacing electrode at the distal tip of said lead;
    a sensor electrode positioned between said pacing electrode and said defibrillation electrode, said sensor electrode spaced from the defibrillation electrode a distance of between 1 and 5 centimeters; and
    means for electrically interfacing said sensor, pacing, and defibrillation electrodes with said implantable pulse generator.

18. The lead of claim 17, wherein said sensor electrode further comprises at least one ring electrode spaced distally from said defibrillation electrode, said at least one ring electrode operative to sense physical parameters in a ventricle of a heart and to produce an output signal corresponding thereto.

19. The lead of claim 18, wherein said lead further comprises a lead body including a defibrillation conductor encased within an insulation material.

20. The lead of claim 18, wherein said defibrillation electrode comprises an electrically conductive coil.

21. The lead of claim 20, wherein said coil of said defibrillation electrode includes a coating deposited on the coil, the material for said coating being selected from the group consisting of platinum black, carbon, titanium and titanium nitride.

22. The lead of claim 20, wherein said coil of said defibrillation electrode is formed from a platinum-iridium wire.

23. The lead of claim 18, wherein said defibrillation electrode is coated with a biocompatible, hypo-inflammatory material.

24. The lead of claim 17, wherein said sensor electrode further comprises at least one ring electrode spaced distally from said defibrillation electrode, said at least one ring electrode operative to sense electrical parameters in a ventricle of a heart and to produce an output signal corresponding thereto.

* * * * *